United States Patent [19]

Creuzet et al.

[11] Patent Number: 4,497,812

[45] Date of Patent: Feb. 5, 1985

[54] 2-AMINO-5-AMINOMETHYL-2-OXAZOLINES, COMPOSITIONS AND USE

[75] Inventors: Marie-Hélène Creuzet, Bordeaux; Claude Feniou, Pessac; Christian Jarry, Artigues près Bordeaux; Gisèle Prat, Talence; Henri Pontagnier, Pessac, all of France

[73] Assignee: Societe Cortial, S.A., Paris, France

[21] Appl. No.: 539,286

[22] Filed: Oct. 5, 1983

[30] Foreign Application Priority Data

Oct. 5, 1982 [FR] France .................. 82 16782
May 19, 1983 [FR] France .................. 83 08477

[51] Int. Cl.³ .................. C07D 263/28; C07D 295/12; A61K 31/42; A61K 31/535
[52] U.S. Cl. .................. 514/211; 514/212; 514/218; 514/237; 514/252; 514/340; 514/364; 514/377; 544/137; 544/360; 544/369; 546/148; 546/193; 546/209; 546/281; 548/233
[58] Field of Search .................. 544/137, 360, 369; 546/148, 193, 209, 281; 548/233; 424/248.56, 250, 263, 258, 267, 272

[56] References Cited

U.S. PATENT DOCUMENTS 3,299,089  1/1967  Zimmermann et al. ............ 548/233

Primary Examiner—Robert W. Ramsuer
Attorney, Agent, or Firm—Oblon, Fisher, Spivak, McClelland & Maier

[57] ABSTRACT

This invention relates to new 2-amino-5-aminomethyl-2-oxazolines, the method of preparing them, and their pharmacological properties making possible their application in cardiovascular, psychotropic, antiinflammatory antiallergic, antihistamine, antiH$_2$ therapy.

These new products have the general formula:

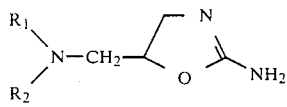

wherein $R_1$ and $R_2$ independently represent an alkyl radical of $C_1$ to $C_4$, or a carbocyclic alkyl radical having less than 4 rings, or a carbocyclic radical having less than 4 rings; $R_1$ and $R_2$ can form, with the nitrogen atom to which they are attached, a 4 to 7 member heterocycle containing 1 or 2 nitrogen atoms, and either 1 or 0 oxygen atoms. This heterocycle can be substituted by R with R being a lower alkyl, allyl, benzyl, pyridyl, phenyl substituted or not by one or more substituents such as halogen, trifluoromethyl, methyl, methoxy, hydroxy.

8 Claims, No Drawings

2-AMINO-5-AMINOMETHYL-2-OXAZOLINES, COMPOSITIONS AND USE

BACKGROUND OF THE INVENTION

1. Field of the Invention

This invention relates to new 2-amino-5-aminomethyl-2-oxazolines, the method of preparing them and their therapeutic application.

2. Description of the Prior Art

2-Amino-2-oxazolines are already known. Thus, 2-amino-5-phenyl-2-oxazoline

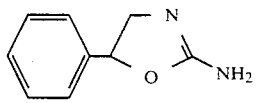

was patented by MacNeil Laboratories Incorporated in France under No. 2448M for its properties of stimulation of the central nervous system and its anorexigenic activity. 2-Amino-5-(3,4-dichlorophenoxymethyl)-2-oxazoline was tested by A. H. Abdallah and coll. for its cardiovascular and anorexigenic activity (Toxicol. appl. Pharmacol. 1973, 26, 513–22; 1973, 25, 344–53) and was patented by the Dow Chemical Company in the United States under U.S. Pat. No. 3,637,726 on Apr. 9, 1970 for its antimicrobial activity.

SUMMARY OF THE INVENTION

The products of this invention are distinguished from already known 2-amino-2-oxazolines by the presence in the 5 position of the ring of an aminomethyl substitution. They exhibit pharmacological properties making possible their application particularly in cardiovascular, psychotropic, antiinflammatory, antiallegric, antihistamine, and antiH$_2$ therapy.

The products of this invention have the general formula

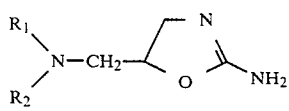
(1)

with $R_1$ and $R_2$ independently represent an alkyl radical (such as $CH_3$, $C_2H_5$, $C_3H_7$, $C_4H_9$) or arylalkyl (such as benzyl) or aryl (such as phenyl); $R_1$ and $R_2$ can form, with the nitrogen atom to which they are attached, a heterocycle such as piperidine, pyrrolidine, morpholine, tetrahydroisoquinoline, or else piperidine or piperazine substituted by R with R being a lower alkyl of $C_1$ to $C_4$, allyl, benzyl, pyridyl, phenyl substituted or not by one or more substitutents such as halogen (for example, chloro, fluoro, bromo), trifluoromethyl, methyl, methoxy, hydroxy.

DESCRIPTION OF THE PREFERRED EMBODIMENTS

These products are prepared by condensation, in a solvent such as methanol, of the cyanamide monosodium derivative on the corresponding N-substituted 1-amino-2,3-epoxypropane

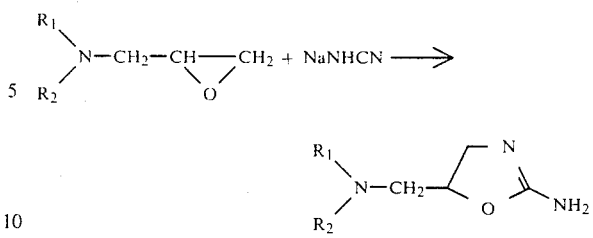

The epoxides are prepared in the standard way by reaction of an amine $HNR_1R_2$ (in which $R_1$ and $R_2$ are defined above) and epichlorohydrin.

The invention will be further illustrated by certain examples and references which are provided for purposes of illustration only and are not intended to limit the present invention.

EXAMPLE 1

Preparation of 2-amino-N,N-5-diethylaminomethyl-2-oxazoline. Formula I with $R_1 = R_2 = C_2H_5$.

One mole of diethylamine is introduced in a reactor equipped with stirring, cooling and a dropping funnel. One mole of epichlorohydrin is introduced, drop by drop, with stirring, while the temperature is kept at 25° C. The stirring is contiued for 5 hours at ambient temperature. Ether (300 cc) is added to the reactor then 48 g of finely powdered soda. The stirring is continued overnight at ambient temperature. The ether phase is filtered and centrifuged. It is washed with 50 cc of water. After decanting, the organic phase is carefully dried on sodium sulfate. The solvent is eliminated under lower pressure and the 1-diethylamino-2,3-epoxypropane is separated by distillation. Yield: 60%, $BP_8 = 44°–48°$ C., $BP_{760} = 157°$ C.

0.2 Mole of the 1-diethylamino-2,3-epoxypropane thus prepared is added, drop by drop, to 12.8 g of the cyanamide monosodium derivative dissolved in 200 cc of anhydrous methanol with vigorous stirring. After 15 hours of stirring at ambient temperature, the methanol is evaporated and the residue picked up with 300 cc of ether. The precipitate is eliminated by filtering. The ether phase is washed twice with 2 cc of water then dried on $Na_2SO_4$ after decanting. The ether is evaporated under low pressure. The resulting oily phase crystallizes after washing with boiling heptane. 2-Amino-5-diethylaminomethyl-2-oxazoline is thus obtained with a yield of 68%. It is purified by recrystallization in heptane.

MP = 90°. Molecular mass 171.

Infrared spectrum: bands $\gamma NH_2$ 3360 cm$^{-1}$, $\gamma C=N$ 1680 cm$^{-1}$.

The NMR of the proton in DMSO(d$_6$) (the chemical shifts are expressed in ppm in relation to the TMS taken as the internal standard): 5.78 ppm, singlet, 2 protons (NH$_2$); 4.67–4.29 ppm, complex mass, 1 proton (H-5 on the oxazoline ring); 3.78–3.05 ppm, complex mass, 2 protons (H in 4 on the oxazoline ring); 2.71–2.31 ppm, complex mass, 6 protons (N—CH$_2$); 0.93 ppm, triplet, 6 protons (CH$_3$—).

EXAMPLE 2

Synthesis of 2-amino-5-(N-butyl-N-methylaminomethyl)-2-oxazoline. Formula I with $R_1 = CH_3$, $R_2 = C_4H_9$.

This product is prepared according to the method described in Example 1. The intermediate product has a boiling point of 44°–50° C. under 0.5 mm of Hg. The final product is purified by recrystallation in hexane.

MP=86° C. Molecular mass 185.

Infrared spectrum: bands $\gamma NH_2$ 3280 cm$^{-1}$, $\gamma C=N$ 1680 cm$^{-1}$.

NMR spectrum in DMSO(d$_6$): 5.8 ppm, singlet, 2 protons (NH$_2$); 4.71–4.33 ppm, complex mass, 1 proton (H in 5 of the oxazoline ring); 3.78–3 ppm, complex mass, 2 protons (H in 4 of the oxazoline ring); 2.62–2.1 ppm, complex mass, 7 protons

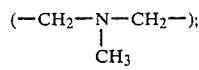

1.55–1.05 ppm, complex mass, 4 protons (C—CH$_2$—CH$_2$—C); 1–0.71 ppm, complex mass, 3 protons (CH$_3$—C).

EXAMPLE 3

Synthesis of 2-amino-5-pyrrolidinomethyl-2-oxazoline. Formula I with R$_1$, R$_2$=—CH$_2$—CH$_2$—CH$_2$—CH$_2$—.

This product is prepared by the method described in Example 1 with the sole difference that the addition reaction of pyrrolidine and epichlorohydrin is performed in the presence of ether. The intermediate epoxide has a boiling point of 73° C. under 25 mm of Hg. The 2-amino-5-pyrrolidinomethyl-2-oxazoline is purified by recrystallization in heptane.

MP=123° C. Molecular mass 169.

Infrared spectrum: bands $\gamma NH_2$ 3300 cm$^{-1}$, $\gamma C=N$ 1685 cm$^{-1}$, NMR spectrum in DMSO(d$_6$): 5.82 ppm, singlet, 2 protons (NH$_2$); 4.71–4.29 ppm, complex mass, 1 proton (H·in 5 of the oxazoline ring); 3.78–3.02 ppm, complex mass, 2 protons (H in 4 of the oxazoline ring); 2.66–2.31 ppm, complex mass, 6 protons (CH$_2$—N); 1.87–1.44 ppm, complex mass, 4 protons (CH$_2$—C).

EXAMPLE 4

Synthesis of 2-amino-5-piperidinomethyl-2-oxazoline. Formula I with R$_1$, R$_2$=CH$_2$—CH$_2$—CH$_2$—CH$_2$—CH$_2$—. This product is prepared by the method described in Example 1. The intermediate epoxide has a boiling point of 51° C. under 0.5 mm of Hg. The final product is purified by recrystallization in heptane.

MP=127° C. Molecular mass 183.

Infrared spectrum: bands $\gamma NH_2$ 3350 cm$^{-1}$, $\gamma C=N$ 1680 cm$^{-1}$.

NMR spectrum in DMSO(d$_6$): 5.8 ppm, singlet, 2 protons (NH$_2$); 4.77–4.35 ppm, complex mass, 1 proton (H in 5 of oxazoline ring); 3.77–2.95 ppm, complex mass, 2 protons (H in 4 of oxazoline ring); 2.58–216 ppm, complex mass, 6 protons (CH$_2$—N); 1.64–1.2 ppm, complex mass, 6 protons (CH$_2$—C).

EXAMPLE 5

Synthesis of 2-amino-5-(4-methylpiperidinomethyl)-2-oxazoline. Formula I with R$_1$, R$_2$=

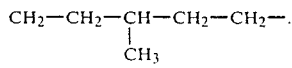

This product is synthesized by the method described in Example 1. The intermediate epoxide has a boiling point of 55° C. under 0.5 mm of Hg. The final product is recrystallized in heptane.

MP=130° C. Molecular mass 197.

Infrared spectrum: bands $\gamma NH_2$ 3260 cm$^{-1}$, $\gamma C=N$ 1690 cm$^{-1}$.

NMR spectrum in DMSO(d$_6$): 5.82 ppm, singlet, 2 protons (NH$_2$); 4.78–4.33 ppm, complex mass, 1 proton (H in 5 of the oxazoline ring); 3.78–3 ppm, complex mass, 2 protons (H in 4 of the oxazoline ring); 3.0–9 ppm, complex mass, 11 protons (CH$_2$—N+H of piperidine ring); 0.87 ppm, doublet, 3 protons (CH$_3$).

EXAMPLE 6

Synthesis of 2-amino-5-(2-ethylpiperidinomethyl)-2-oxazoline. Formula I with R$_1$, R$_2$=

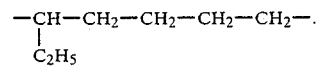

This product is synthesized by the method described in Example 1. The intermediate epoxide has a boiling point of 83° C. under 0.5 mm of Hg. The final product is recrystallized in heptane.

MP=114° C. Molecular mass 211.

Infrared spectrum: bands $\gamma NH_2$ 3350 cm$^{-1}$, $\gamma C=N$ 1680 cm$^{-1}$.

NMR spectrum in DMSO(d$_6$): 5.82 ppm, singlet, 2 protons (NH$_2$); 4.75–4.33 ppm, complex mass, 1 proton (H in 4 of the oxazoline ring); 3–2.05 ppm, complex mass, 5 protons (CH$_2$—N+CH—N); 1.77–1.11 ppm, complex mass, 8 protons (CH$_2$—C); 0.8 ppm, triplet, 3 protons (CH$_3$).

EXAMPLE 7

Synthesis of 2-amino-5-morpholinomethyl-2-oxazoline. Formula I with R$_1$, R$_2$=CH$_2$—CH$_2$—O—CH$_2$—CH$_2$—.

This product is synthesized by the method described in Example 1. The intermediate epoxide has a melting point of 67° C. under 0.5 mm of Hg. The final product is purified by recrystallization in CCl$_4$.

MP=152° C. Molecular mass 185.

Infrared spectrum: bands $\gamma NH_2$ 3340 cm$^{-1}$, $\gamma C=N$ 1680 cm$^{-1}$.

NMR spectrum in DMSO(d$_6$): 5.84 ppm, singlet, 2 protons (NH$_2$), 4.82–4.38 ppm, complex mass, 1 proton (H in 5 of the oxazoline ring); 3.77–3 ppm, complex mass, 2 protons (H in 4 of the oxazoline ring); 3.55 ppm, triplet, 4 protons (CH$_2$—O); 2.58–2.29 ppm, complex mass, 6 protons (CH$_2$—N).

EXAMPLE 8

Synthesis of 2-amino-5-(N-methyl-N-phenylaminomethyl)-2-oxazoline. Formula I with R$_1$=CH$_3$, R$_2$=C$_6$H$_5$.

This product is synthesized by the method described in Example 1 except throughout the reaction between the N-methylaniline and epichlorohydrin the reaction mixture is heated to 50° C. The intermediate epoxide has a boiling point of 105° C. under 0.5 mm of Hg. The final product is in the form of an undistillable oil. Molecular mass 2.5.

Infrared spectrum: bands $\gamma NH_2$ 3340 cm$^{-1}$, $\gamma C=N$ 1680 cm$^{-1}$.

NMR spectrum in DMSO(d$_6$): 7.4–6.4 ppm, complex mass, 5 protons (H of the aromatic ring); 5.65 ppm, complex mass, 2 protons (NH$_2$); 4.89–4.44 ppm, 4–3.05 ppm, complex mass, 4 protons (CH$_2$); 3 ppm, triplet, 3 protons (CH$_3$).

EXAMPLE 9

Synthesis of 2-amino-5-(N-benzyl-N-methylaminomethyl)-2-oxazoline. Formula I with R$_1$=CH$_2$C$_6$H$_5$, R$_2$=CH$_3$.

This product is synthesized by the method described in Example 1. The final product is recrystallized in heptane.

MP=98° C. Molecular mass 219.

Infrared spectrum: bands $\gamma$NH$_2$ 3490 cm$^{-1}$, $\gamma$C=N 1680 cm$^{-1}$.

NMR spectrum in CDCl$_3$: 7.22 ppm, singlet, 5 protons (aromatic H); 4.84 ppm, singlet, 2 protons (NH$_2$); 4.82–4.48 ppm, complex mass, 1 proton (H in 5 of oxazoline ring); 3.88–3.18 ppm, complex mass, 2 protons (H in 4 of the oxazoline ring); 3.53 ppm, singlet, 2 protons (benzyl CH$_2$); 2.82–2.17 ppm, complex mass, 2 protons (CH$_2$ in 5 on the oxazoline ring); 2.29 ppm, singlet, 3 protons (NCH$_3$).

EXAMPLE 10

Synthesis of 2-amino-(4-methylpiperazinyl)-5-methyl-2-oxazoline. Formula I with R$_1$NR$_2$=

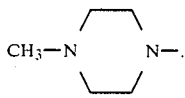

0.25 mole (23.13 g) of epichlorohydrin is added, drop by drop, to a solution of 0.25 mole of N-methylpiperazine in 200 cc of ether. The reaction mixture is kept at a temperature below 35° C. during the addition; it is then heated in a double boiler for two hours at the boiling point of the ether. 10 g (0.25 mole) of finely powdered soda are added. The precipitate is eliminated by filtering.

The ether phase is washed twice with 2 cc of water then dried on Na$_2$SO$_4$. The solvent is eliminated and the 1-methylpiperazinyl-2,3-epoxypropane is separated by distillation.

Boiling point under 1.33 mb=100° C.

The purity of this product is checked in infrared by disappearance of the NH band of the starting amine and the appearance of a C—O—C band at 930 cm$^{-1}$. 0.1 mole (6.4 g) of cyanamide monosodium derivative in solution in 100 cc of methanol is added to 0.1 mole (15.6 g) of N-methyl-1-piperazinyl-2,3-epoxypropane dissolved in 150 cc of methanol. After 15 hours of stirring at ambient temperature the methanol is evaporated and the residue picked up in 200 cc of ethyl ether. The precipitate is eliminated by filerting. The ether phase is quickly washed with 5 cc of water then dried on Na$_2$SO$_4$. The ether is evaporated under low pressure. The 2-amino-N-methyl-5-piperazinyll-2-oxazoline is collected in the form of an oil that solidifies then is recrystallized in CCl$_4$.

MP=130° C. Yield 61%. Molecular mass 198. Microanalysis: calculated C 9.09%, H 54.54%, N 28.28%; found C 9.13, H 54.41%, N 28.19%.

IR spectrum: bands $\gamma$NH$_2$ 3300 and 3180 cm$^{-1}$, $\gamma$C=N 1680 cm$^{-1}$.

NMR of proton in CDl$_3$: 2.1–3.0 ppm, 13 protons, complex mass, N N—CH$_2$+CH$_3$ at 2.3 ppm; 3.1–4.1 ppm, 2 protons, complex mass, oxazoline CH$_2$; 4.4–5.0 ppm, 1 proton, complex mass, CHO; 5.4 ppm, 2 protons, wide peak, NH$_2$, interchangeable with D$_2$O.

EXAMPLE 11

Synthesis of 2-amino-(4-phenylpiperazinyl)-5-methyl-2-oxazoline. Formula I with R$_1$NR$_2$=

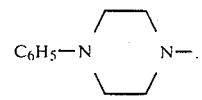

This product is prepared by the method described in Example 10. The intermediate epoxide is obtained in crystallized form. MP=89° C.; (recrystallization solvent: heptane).

The final product is purified by recrystallization in heptane. MP=89° C.; (recrystallization solvent: heptane).

The final product is purified by recrystallization in heptane. MP=174° C. Yield 51%. Molecular mass 260. Microanalysis: calculated C 7.69%, H 64.62%, N 21.54%; found C 7.60%, H 64.40%, N 21.34%. IR spectrum: bands $\gamma$NH$_2$ 3330 and 3180 cm$^{-1}$, band $\gamma$C=N 1670 cm$^{-1}$. NMR of proton in CDCl$_3$: 2.3–4.1 ppm, 12 protons, complex mass, 6 CH$_2$; 4.5–5.0 ppm, 3 protons, complex mass, CHO+NH$_2$, interchangeable with D$_2$O; 6.7–7.5 ppm, 5 protons, complex mass, aromatic protons.

EXAMPLE 12

Synthesis of 2-amino-(4-benzylpiperidinyl)-5-methyl-2-oxazoline. Formula I with R$_1$NR$_2$=

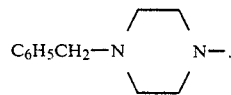

This product is synthesized by the method described in Example 10. Its yield is 46%. It is purified by recrystallization in heptane.

MP=114° C. Molecular mass 273.

IR spectrum: bands $\gamma$NH$_2$ 3320 and 3160 cm$^{-1}$, $\gamma$C=N 1685 cm$^{-1}$.

NMR of the proton in CDCl$_3$: 1.1–4.1 ppm, 15 protons, complex mass, 7 CH$_2$+piperidinic CH; 4.4–5.0 ppm, 1 proton, complex mass, CHO; 5.1 ppm, 2 protons, wide peak, NH$_2$, interchangeable with D$_2$O; 6.9–7.4 ppm, 5 protons, complex mass, aromatic protons.

EXAMPLE 13

Synthesis of 2-amino-(4-benzylpiperazinyl)-5-methyl-2-oxazoline. Formula I with R$_1$NR$_2$=

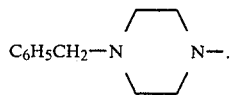

This product is synthesized as in the method described in Example 10. Its yield is 48%. It is purified by recrystallization in heptane.

MP=96° C. Molecular mass 274. Microanalysis: calculated C 8.03%, H 65.69%, N 20.44%; found C 8.06%, H 64.93%, N 20.34%.

IR spectrum: bands $\gamma NH_2$ 3310 and 3160 cm$^{-1}$, $\gamma C=N$ 1680 cm$^{-1}$.

NMR of proton in CDCl$_3$: 2.2–3.0 ppm, 10 protons, complex mass

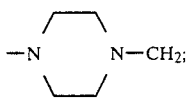

3.1–4.1 ppm, protons, complex mass, benzyl CH$_2$+oxazolinic CH$_2$: 4.4–5.0 ppm, 3 protons, complex mass, CHO+NH$_2$ interchangeable with D$_2$O; 7.2–7.4 ppm, 8 protons, complex mass, aromatic protons.

EXAMPLE 14

Synthesis of 2-amino-(4-allylpiperazinyl)-5-methyl-2-oxazoline. Formula I with R$_1$NH$_2$=

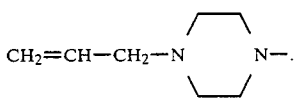

This product is synthesized by the method described in Example 10. The intermediate epoxide has a boiling point of 67° C. under 1 mb. The final product obtained with a yield of 43% is purified by recrystallization in heptane.

MP=99° C. Molecular mass 224. Microanalysis: calculated C 8.93%, H 58.93%, N 25%, fond C 8.93%, H 58.01%, N 24.99%.

IR spectrum: bands $\gamma NH_2$ 3200 and 3160 cm$^{-1}$, $\gamma C=H$ 1690 cm$^{-1}$.

NMR of the proton in CDCl$_3$; 2.2–4.1 ppm, 14 protons, complex mass,

+oxazoline CH$_2$; 4.4–6.3 ppm, 6 protons, complex mass; CH$_2$=CH—+CHO+NH$_2$ at 4.9 ppm interchangeable with D$_2$O.

The pharmacological properties of the products of this invention are set forth below.

The toxicity was determined in mice for various ways of administraion. Table I gives the percentages of mortality as a function of the doses administered.

TABLE I

| Products of examples | Percentage of mortality at does of | | | |
|---|---|---|---|---|
| | orally | | intraperitoneally | |
| | 300 mg/kg | 200 mg/kg | 200 mg/kg | 100 mg/kg |
| 1 | 0 | | 0 | |
| 2 | 0 | | 100 | 0 |
| 3 | 0 | | 100 | 0 |
| 4 | 33 | 0 | 100 | 0 |
| 5 | 0 | | 100 | 0 |
| 6 | 0 | | 0 | |
| 7 | 100 | | | |
| 10 | 0 | | 0 | |
| 11 | 0 | | 0 | |
| 12 | 100 | 0(1) | 100 | 0 |
| 13 | 0 | | 100 | 0 |
| 14 | 0 | | 0 | |

(1): 100 mg/kg

The product of Example 1 shows, after iv administration in mice, an LD$_{50}$ of 128 (116–142 mg/kg).

Antihistaminic activity antiH$_2$ was determined in vitro on the right auricle of a guinea pig beating spontaneously. Thus, the products of Example 1, 2, 6, 13 inibit at more than 50% at a concentration of 100 microg/ml the chronotropic effect induced by 5 microg/ml of histamine, without exhibiting intrinsic chronotropic effect. The product of Example 14 exhibits this activity at a concentration of 50 microg/ml.

The positive inotropic activity was determined in vitro on the right auricle of a guinea pig stimulated electrically. The product of Example 1 caused, at 100 microg/ml, 100% increase of the auricle contractile force.

The antiallergic activity was determined in rats in the cutaneous passive anaphylaxis test. The animals sensitized by an intradermic injection of IgE immediately received, after administration of the product to be tested, an intravenous injection of ovalbumin and Evans blue. The products of Examples 3 and 4 caused, at 10 mg/kg, 53 and 60% respectively inhibition of the Evans blue spot. The product of Example 1 caused 60% inhibition when it was administered at 100 mg/kg per os.

The diuretic activity was determined in rats subjected to a hydric regimen and evaluated by the ratio of sodium excreted in the treated animals to the sodium excreted in control animals. The products of Examples 3 and 7 multiplied the sodium excretion by 4.2 and 4.9 respectively at a dose of 20 mg/kg per os.

The hypocholesterolemic activity was determined in mice subjected to a regimen rich in cholesterol and cholic acid for 7 days. After administration per os of the production of Example 6 in a dose of 400 mg/kg, a 21% reduction of cholesterolemia was noted on the 6th and 7th days. This drop in cholesterolemia was accompanied by a 20% reduction of the HDL-VLDL fraction, the HDL/cholesterol ratio being equal to 1.01.

The antidepressive psychotropic activities were brought out in the following tests. The products of Examples 11 and 12, administered in an oral dose of 100 mg/kg, potentiated the toxicity of yohimbine. The product of Example 11, administered in 50 mg/kg per os, inhibited ptosis induced by reserpine.

The antiinflammatory activity was brought out in the carrageenan edema test in rats. The product of Example 11, administered per os in a dose of 100 mg/kg, caused a 35% inhibition of carrageenan adema after 4 hours. In a dose of 200 mg/kg administered per os this product is very slightly ulcerigenic.

The antihistaminic activity antiH$_1$ was determined in vitro on guinea pig ileum. The products of Example 11 and 13 inhibited at more than 80% the contractions of the guinea pig ileum induced by histamine when they are used in concentrations of 25 and 100 microg/ml respectively.

In vitro the product of Example 11 caused, in a concentration of 25 microg/ml, 80% inhibition of the contractions induced by serotinin on guinea pig ileum.

The antiulcerigenic activity was shown in the stress ulcer test. The product of Example 11, administered in a dose of 25 mg/kg per os, caused an 88% inhibition of the stress ulcer in rats.

In the model of the spontaneously hypertensive rat, the product of Example 13, administered orally in a dose of 100 mg/kg, caused a drop in systolic pressure of 14 and 15% respectively after two and four hours. The product of Example 14, administered in a dose of 100 mg/kg under the same conditions, caused a reduction of 21% of the systolic pressure after six hours.

Considering their pharmacological activities, joined with a relatively slight toxicity, the products which are the object of this invention can be used in human and animal therapy. Thus, when associated with suitable excipients, they can be used in the treatment of depressive states, inflammatory and edematous states, asthma attacks or any condition of allergy, arterial hypertension, gastric hypersecretions, gastroduodenal ulcers. Their positive inotropic activity makes it possible to use them in the treatment of acute or chronic cardiac failures. Their diuretic properties make it possible to use them in the treatment of edemas and water sodium retentions. Their hypolipidemic properties make it possible to use them in hypercholesterolemias and hypertriglyceridemias resistant in the regimen.

They will be administered in the form of dragees, tablets, syrup, ampules, rectally as suppositories, intramuscularly or intravenously or topically as ointments or gels. The dose will vary, depending on the indication and patient, from 1 to 100 mg/d in 2 to 6 doses orally, 1 to 100 mg/d in 1 or 2 doses rectally, from 0.5 to 50 mg parenterally. They can also be used for inhalation, for example, as sprays.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound having the general formula:

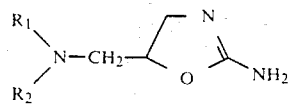

wherein $R_1$ and $R_2$ independently represent an alkyl radical of $C_1$ to $C_4$, or a carbocyclic alkyl radical having less than 4 rings, or a carbocyclic radical having less than 4 rings;

$R_1$ and $R_2$ can form, with the nitrogen atom to which they are attached, a 4 to 7 member heterocycle containing 1 or 2 nitrogen atoms, and either 1 or 0 oxygen atoms, said heterocycle can be substituted by R with R being an alkyl radical of $C_1$ to $C_4$, a carbocyclic alkyl radical having less than 4 rings, allyl, a 5 or 6 member heterocycle containing 1 nitrogen, or a carbocyclic radical having less than 4 rings substituted or not by one or more substituents such as halogen, trihalomethyl alkyl of $C_1$ to $C_4$, alkyloxy of $C_1$ to $C_4$, or hydroxy.

2. The compound of claim 1, wherein $R_1$ and $R_2$ are independently chosen from the group consisting of methyl, ethyl, n-propyl, iso-propyl, n-butyl, sec-butyl, iso-butyl, tert-butyl, benzyl, and phenyl.

3. The compound of claim 1, wherein said heterocycle formed by $R_1$ and $R_2$ is chosen from the group consisting of piperidine, pyrrolidone, morpholine, tetrahydroisoquinoline, and piperazine.

4. A pharmaceutical or veterinary composition characterized in that it contains as active principle at least a product as in claim 1 in association with a pharmaceutical vehicle or suitable excipient.

5. A method for cardiovascular therapy which comprises administration of an effective amount of a compound of claim 1.

6. A method for allergology therapy which comprises administration of an effective amount of a compound of claim 1.

7. A method for gastroduodenal ulcer therapy which comprises administration of an effective amount of a compound of claim 1.

8. A method for psychotropic therapy which comprises administration of an effective amount of a compound of claim 1.

* * * * *